United States Patent
Morrow et al.

(10) Patent No.: US 12,171,773 B2
(45) Date of Patent: *Dec. 24, 2024

(54) INHIBITING INFLAMMATION WITH MILK OLIGOSACCHARIDES

(71) Applicants: Children's Hospital Medical Center, Cincinnati, OH (US); The General Hospital Corporation, Boston, MA (US); Instituto Nacional de Ciencias Medicas Y Nutricion, Mexico City (MX)

(72) Inventors: Ardythe L. Morrow, Cincinnatti, OH (US); David S. Newburg, Newtonville, MA (US); Guillermo M. Ruiz-Palacios, Mexico City (MX)

(73) Assignees: Children's Hospital Medical Center, Cincinnati, OH (US); The General Hospital Corporation, Boston, MA (US); Instituto Nacional de Ciencias. Medicas Y Nutricion, Mexico City (MX)

(*) Notice: Subject to any disclaimer, the term of this patent is extended or adjusted under 35 U.S.C. 154(b) by 0 days.

This patent is subject to a terminal disclaimer.

(21) Appl. No.: 17/736,468

(22) Filed: May 4, 2022

(65) Prior Publication Data

US 2023/0101412 A1   Mar. 30, 2023

Related U.S. Application Data

(63) Continuation of application No. 17/333,614, filed on May 28, 2021, now Pat. No. 11,324,765, which is a continuation of application No. 15/998,799, filed on Aug. 16, 2018, now Pat. No. 11,058,697, which is a continuation of application No. 14/700,232, filed on Apr. 30, 2015, now Pat. No. 10,098,903, which is a continuation of application No. 13/382,323, filed as application No. PCT/US2010/040895 on Jul. 2, 2010, now Pat. No. 9,034,847.

(60) Provisional application No. 61/223,145, filed on Jul. 6, 2009.

(51) Int. Cl.
| | | |
|---|---|---|
| A61K 31/7016 | (2006.01) | |
| A23L 33/00 | (2016.01) | |
| A61K 31/702 | (2006.01) | |
| A61K 35/20 | (2006.01) | |
| A61K 47/50 | (2017.01) | |
| A61K 47/61 | (2017.01) | |
| A61K 47/62 | (2017.01) | |

(52) U.S. Cl.
CPC .......... A61K 31/7016 (2013.01); A23L 33/40 (2016.08); A61K 31/702 (2013.01); A61K 47/62 (2017.08); A61K 35/20 (2013.01); A61K 47/50 (2017.08); A61K 47/61 (2017.08)

(58) Field of Classification Search
CPC ............ A61P 1/00–18; A61K 31/7016; A61K 31/702; A61L 33/40
See application file for complete search history.

(56) References Cited

U.S. PATENT DOCUMENTS

| | | |
|---|---|---|
| 3,681,373 A | 8/1972 | Adams et al. |
| 5,470,843 A | 11/1995 | Stahl et al. |
| 5,474,986 A | 12/1995 | Magnusson et al. |
| 5,484,773 A | 1/1996 | Heerze et al. |
| 5,576,300 A | 11/1996 | Mukerji et al. |
| 5,635,606 A | 6/1997 | Heerze et al. |
| 5,700,671 A | 12/1997 | Prieto et al. |
| 5,892,070 A | 4/1999 | Prieto et al. |
| 5,919,913 A | 7/1999 | Nuyens et al. |
| 6,045,854 A | 4/2000 | Prieto et al. |
| 6,126,961 A | 10/2000 | Kross |
| 6,132,710 A | 10/2000 | Panigrahi et al. |
| 6,146,670 A | 11/2000 | Prieto et al. |
| 6,204,431 B1 | 3/2001 | Prieto et al. |
| 6,291,435 B1 | 9/2001 | Yanmaele et al. |
| 6,540,999 B1 | 4/2003 | Ham et al. |
| 7,871,785 B2 | 1/2011 | Morrow et al. |
| 7,893,041 B2 | 2/2011 | Morrow et al. |
| 8,314,061 B2 | 11/2012 | Morrow et al. |
| 8,574,850 B2 | 11/2013 | Morrow et al. |
| 9,034,847 B2 | 5/2015 | Morrow et al. |
| 9,132,142 B2 | 9/2015 | Morrow et al. |
| 9,132,143 B2 | 9/2015 | Morrow et al. |
| 10,098,903 B2 | 10/2018 | Morrow et al. |
| 2002/0019991 A1 | 2/2002 | Prieto et al. |
| 2002/0058313 A1 | 5/2002 | Renkonen et al. |
| 2002/0115839 A1 | 8/2002 | Meyers et al. |
| 2003/0036070 A1 | 2/2003 | Chakravarti |

(Continued)

FOREIGN PATENT DOCUMENTS

| | | |
|---|---|---|
| EP | 0870841 A1 | 10/1998 |
| EP | 1199364 A2 | 4/2002 |

(Continued)

OTHER PUBLICATIONS

Vavricka, S. et al."New insights in to the pathogenesis of Crohn's disease . . . " Swiss Med. Wkly, vol. 139, pp. 527-534. (Year: 2009).*
[No Author Listed], Certified copy of priority document U.S. Appl. No. 61/223,145 (Priority Document of European Application No. EP10797669.8, now EP2451462B1). Jul. 12, 2010. 31 pages.
[No Author Listed], Declaration of David S. Newburg, Ph.D in European Application No. EP10797669.8, now EP2451462B1, dated Aug. 6, 2019. 4 pages.
[No Author Listed], Declaration of John McCoy, Ph.D in European Application No. EP10797669.8, now EP2451462B1, dated Aug. 17, 2019. 2 pages.

(Continued)

*Primary Examiner* — Leigh C Maier
(74) *Attorney, Agent, or Firm* — Bose Mckinney & Evans LLP

(57) ABSTRACT

A method of inhibiting inflammation with milk oligosaccharides or glycoconjugates containing the oligosaccharides.

21 Claims, 3 Drawing Sheets

(56) References Cited

U.S. PATENT DOCUMENTS

| | | |
|---|---|---|
| 2004/0131659 A1 | 7/2004 | Gibson |
| 2006/0040893 A1 | 2/2006 | Harn et al. |
| 2007/0020660 A1 | 1/2007 | Burczynski et al. |
| 2007/0134251 A1 | 6/2007 | Ashkenazi et al. |
| 2007/0275881 A1 | 11/2007 | Morrow et al. |
| 2009/0098240 A1 | 4/2009 | Mills |
| 2009/0169535 A1 | 7/2009 | Marth |
| 2011/0177035 A1 | 7/2011 | Morrow et al. |
| 2011/0207659 A1 | 8/2011 | Morrow et al. |
| 2012/0202753 A1 | 8/2012 | Morrow et al. |
| 2012/0294840 A1 | 11/2012 | Newburg et al. |
| 2014/0140970 A1 | 5/2014 | Morrow et al. |
| 2014/0271562 A1 | 9/2014 | Garcia-Rodenas et al. |
| 2015/0079055 A1 | 3/2015 | Morrow et al. |
| 2015/0265661 A1 | 9/2015 | Newburg et al. |
| 2015/0376696 A1 | 12/2015 | Morrow et al. |
| 2016/0143928 A1 | 5/2016 | German et al. |
| 2018/0153915 A1 | 6/2018 | Morrow et al. |

FOREIGN PATENT DOCUMENTS

| | | |
|---|---|---|
| EP | 2631650 A1 | 8/2013 |
| EP | 2768311 B1 | 2/2018 |
| EP | 2768313 B2 | 1/2019 |
| JP | 2009532372 A | 9/2009 |
| WO | WO 1992/018610 A2 | 10/1992 |
| WO | WO 1994/018986 A1 | 9/1994 |
| WO | WO 1995/024495 A1 | 9/1995 |
| WO | WO 1999/031224 A2 | 6/1999 |
| WO | WO 1999/056754 A1 | 11/1999 |
| WO | WO 2002/043578 A2 | 6/2002 |
| WO | WO 2004/041291 A1 | 5/2004 |
| WO | WO 2005/039319 A2 | 5/2005 |
| WO | WO 2005/055944 A2 | 6/2005 |
| WO | WO 2005/110121 A1 | 11/2005 |
| WO | WO 2006/017859 A2 | 2/2006 |
| WO | WO 2006/091103 A2 | 8/2006 |
| WO | WO 2007/087468 A2 | 8/2007 |
| WO | WO 2007/090894 A1 | 8/2007 |
| WO | WO 2009/033011 A1 | 3/2009 |
| WO | WO 2009/077352 A1 | 6/2009 |
| WO | WO 2010/065652 A1 | 6/2010 |
| WO | WO 2011/005681 A1 | 1/2011 |
| WO | WO 2013/057062 A1 | 4/2013 |
| WO | WO 2017/046711 A1 | 3/2017 |

OTHER PUBLICATIONS

[No Author Listed], definition for term "entero-"; The Free Dictionary. Accessible at thefreedictionary.com/entero-. Retrieved Jan. 13, 2016. 1 page.

[No Author Listed], definition for term "-itis"; The Free Dictionary. Accessible at thefree dictionary.com/-itis. Retrieved Jan. 13, 2016. 1 page.

[No Author Listed], Dorland's Illustrated Medical Dictionary, 27th Edition, 1988, p. 228.

[No Author Listed], Inflammatory Bowel Disease. Wikipedia. Oct. 26, 2018. 14 pages. Accessible at en.wikipedia.org/wiki/inflammatory_bowel_disease.

[No Author Listed], Necrotizing enterocolitis. MedlinePlus. Oct. 26, 2018. 3 pgaes. Accessible at medlineplus.gov/ency/article/001148.htm.

[No Author Listed], Necrotizing enterocolitis. Wikipedia. Oct. 26, 2018. 5 pages. Accessible at en.wikipedia.org/wiki/Necrotizing_enterocolitis.

[No Author Listed], Notice of Opposition to European Application No. EP107797669.8, now EP2451462B1, dated Jun. 5, 2018. N.V. Nutricia. 182 pages.

[No Author Listed], Notice of Opposition to European Application No. EP107797669.8, now EP2451462B1, dated Jun. 6, 2018. Grunecker. 151 pages.

[No Author Listed], Notice of Opposition to European Application No. EP107797669.8, now EP2451462B1, dated Nov. 28, 2019. Grunecker. Brief.

[No Author Listed], Post-published evidence submitted during the Examination procedure (letter dated Jun. 11, 2014).

[No Author Listed], Quantikine Total Adiponectin ELISA Kit. Accessible at funakoshi.co.jp/contents/6797. Last accessed Dec. 18, 2014. 3 pages.

Akiho et al., Low-grade inflammation plays a pivotal role in gastrointestinal dysfunction in irritable bowel syndrome. World J Gastrointest Pathophysiol. Aug. 15, 2010; 1(3):97-105.

Albermann et al., Synthesis of the milk oligosaccharide 2'-fucosyllactose using recombinant bacterial enzymes. Carbohydr Res. Aug. 23, 2001;334(2):97-103.

Anderson et al., Improved method for the isolation of 2' fucosyllactose from human milk. J Chromatogr. Jun. 26, 1981;211(1):170-4.

Barclay et al., Systematic review: the role of breastfeeding in the development of pediatric inflammatory bowel disease. J Pediatr. Sep. 2009;155(3):421-6. Epub May 22, 2009.

Bin-Nun et al., Oral probiotics prevent necrotizing enterocolitis in very low birth weight neonates. J Pediatr. Aug. 2005;147(2):192-6.

Blackwell, The role of ABO blood groups and secretor status in host defences. FEMS Microbiol Immunol. Jun. 1989;1(6-7):341-9.

Bode et al., Human milk oligosaccharides reduce platelet-neutrophil complex formation leading to a decrease in neutrophil beta 2 integrin expression. J Leukoc Biol. Oct. 2004;76(4):820-6. Epub Jul. 7, 2004.

Bode et al., Inhibition of monocyte, lymphocyte, and neutrophil adhesion to endothelial cells by human milk oligosaccharides. Thromb Haemost. Dec. 2004;92(6):1402-10.

Bode, Recent advances on structure, metabolism, and function of human milk oligosaccharides. J Nutr. Aug. 2006;136(8):2127-30.

Boehm et al., Oligosaccharides from milk. J Nutr. Mar. 2007;137(3 Suppl 2):847S-9S.

Boehm et al., Supplementation of a bovine milk formula with an oligosaccharide mixture increases counts of faecal bifidobacteria in preterm infants. Arch Dis Child Fetal Neonatal Ed. May 2002;86(3):F178-81.

Brown et al., Altered immune system glycosylation causes colitis in alpha1,2-fucosyltransferase transgenic mice. Inflamm Bowel Dis. Sep. 2004;10(5):546-56.

Buescher. Anti-inflammatory characteristics of human milk: how, where, why. Adv Exp Med Biol. 2001;501:207-22.

Caplan et al., Bifidobacterial supplementation reduces the incidence of necrotizing enterocolitis in a neonatal rat model. Gastroenterology. Sep. 1999;117(3):577-83.

Catala et al., Oligofructose contributes to the protective role of bifidobacteria in experimental necrotising enterocolitis in quails. J Med Microbiol. Jan. 1999;48(1):89-94.

Chaturvedi et al., Fucosylated human milk oligosaccharides vary between individuals and over the course of lactation. Glycobiology. May 2001;11(5):365-72.

Chaturvedi et al., Milk oligosaccharide profiles by reversed-phase HPLC of their perbenzoylated derivatives. Anal Biochem. Aug. 15, 1997;251(1):89-97.

Chen et al., Probiotics and prebiotics: role in clinical disease states. Adv Pediatr. 2005;52:77-113.

Cheromcha et al., Neonatal necrotizing enterocolitis. Inflammatory bowel disease of the newborn. Dig Dis Sci. Mar. 1988;33(3 Suppl):78S-84S. Abstract.

Chirico et al., Antiinfective properties of human milk. J Nutr. Sep. 2008;138(9):1801S-1806S.

Clarke et al., Irritable bowel syndrome: towards biomarker identification. Trends Mol Med. Oct. 2009; 15(10):478-89. Epub Oct. 5, 2009.

Claud, Neonatal Necrotizing Enterocolitis—Inflammation and Intestinal Immaturity. Antiinflamm Antiallergy Agents Med Chem. Sep. 2009;8(3):248-259. Abstract.

Collins et al., Probiotics, prebiotics, and synbiotics: approaches for modulating the microbial ecology of the gut. Am J Clin Nutr. May 1999;69(5):1052S-1057S. Review.

(56) References Cited

OTHER PUBLICATIONS

Cooper et al., Immunohistologic study of ulcerative colitis with monoclonal antibodies against tumor-associated and/or differentiation antigens. Gastroenterology. Sep. 1988;95(3):686-93.
Coppa et al., Human milk oligosaccharides inhibit the adhesion to Caco-2 cells of diarrheal pathogens: *Escherichia coli*, Vibrio cholerae, and Salmonella fyris. Pediatr Res. Mar. 2006;59(3):377-82.
Cordon-Cardo et al., Immunohistologic expression of blood-group antigens in normal human gastrointestinal tract and colonic carcinoma. Int J Cancer. May 15, 1986;37(5):667-76.
Cregg et al., Recombinant protein expression in Pichia pastoris. Mol Biotechnol. Sep. 2000;16(1):23-52.
Cremon et al., Mucosal immune activation in irritable bowel syndrome: gender-dependence and association with digestive symptoms. Am J Gastroenterol. Feb. 2009; 104(2):392-400. Epub Jan. 13, 2009.
D'Adamo et al., Metabolic and immunologic consequences of ABH secretor and Lewis subtype status. Altern Med Rev. Aug. 2001;6(4):390-405.
Daddaoua et al., Goat milk oligosaccharides are anti-inflammatory in rats with hapten-induced colitis. J Nutr. Mar. 2006;136(3):672-6.
Dai et al., Role of oligosaccharides and glycoconjugates in intestinal host defense. J Pediatr Gastroenterol Nutr. 2000;30 Suppl 2:S23-33.
De Giorgio et al., Is irritable bowel syndrome an inflammatory disorder? Curr Gastroenterol Rep. Aug. 2008;10(4):385-90.
Dean et al., The VRG4 gene is required for GDP-mannose transport into the lumen of the Golgi in the yeast, *Saccharomyces cerevisiae*. J Biol Chem. Dec. 12, 1997;272(50):31908-14.
Dinan et al., Hypothalamic-pituitary-gut axis dysregulation in irritable bowel syndrome: plasma cytokines as a potential biomarker? Gastroenterology. Feb. 2006;130(2):304-11.
Dunlop et al., Relative importance of enterochromaffin cell hyperplasia, anxiety, and depression in postinfectious IBS. Gastroenterology. Dec. 2003;125(6):1651-9.
Eiwegger et al., Human milk-derived oligosaccharides and plant-derived oligosaccharides stimulate cystokine production of cord blood T-cells in vitro. Pediatr Res. Oct. 2004;56(4):536-40. Epub Aug. 4, 2004.
Ewaschuk et al., Probiotics and prebiotics in chronic inflammatory bowel diseases. World J Gastroenterol. Oct. 7, 2006;12(37):5941-50.
Fortier et al., The viral mimic, polyinosinic:polycytidylic acid, induces fever in rats via an interleukin-1-dependent mechanism. Am J Physiol Regul Integr Comp Physiol. Oct. 1, 2004;287(4):R759-66.
Frost et al., The importance of pro-inflammatory signaling in neonatal necrotizing enterocolitis. Semin Perinatol. Apr. 2008;32(2):100-6. doi: 10.1053/j.semperi.2008.01.001.
Gao et al., Identification of a conserved motif in the yeast golgi GDP-mannose transporter required for binding to nucleotide sugar. J Biol Chem. Feb. 9, 2001;276(6):4424-32. Epub Nov. 6, 2000.
Gnoth et al., Investigations of the in vitro transport of human milk oligosaccharides by a Caco-2 monolayer using a novel high performance liquid chromatography-mass spectrometry technique. J Biol Chem. Sep. 14, 2001;276(37):34363-70. Epub Jun. 21, 2001.
Gokmen-Polar et al., Elevated protein kinase C betaII is an early promotive event in colon carcinogenesis. Cancer Res. Feb. 15, 2001;61(4):1375-81.
Grazioso et al., Anti-inflammatory effect of human milk feeding on chemically induced colitis in rats. Pediatric Research. 1996;39;119. Abstract.
Grazioso et al., Anti-inflammatory effects of human milk on chemically induced colitis in rats. Pediatr Res. Nov. 1997; 42(5):639-43.
Grollman et al., Correlation Between Secretor Status and the Occurrence of 2'-Fucosyllactose in Human Milk. Biochem Biophys Res Comm. May 25, 1967;28(1):50-53.
Grover et al., The functional-organic dichotomy: postinfectious irritable bowel syndrome and inflammatory bowel disease-irritable bowel syndrome. Clin Gastroenterol Hepatol. Jan. 2009;7(1):48-53. Epub Sep. 3, 2008.

Gwee et al., Increased rectal mucosal expression of interleukin 1beta in recently acquired post-infectious irritable bowel syndrome. Gut. Apr. 2003;52(4):523-6.
Hällström et al., Effects of mode of delivery and necrotising enterocolitis on the intestinal microflora in preterm infants. Eur J Clin Microbiol Infect Dis. Jun. 2004;23(6):463-70. Epub May 27, 2004.
Hanisch et al., Structures of acidic O-linked polylactosaminoglycans on human skim milk mucins. Glycoconj J. 1990;7(6):525-43.
Hanisch et al., Structures of neutral O-linked polylactosaminoglycans on human skim milk mucins. A novel type of linearly extended poly-N-acetyllactosamine backbones with Gal beta(1-4)GlcNAc beta(1-6) repeating units. J Biol Chem. Jan. 15, 1989;264(2):872-83.
Haynes et al., Proteome analysis: biological assay or data archive? Electrophoresis. Aug. 1998;19(11):1862-71.
Heneghan et al., Effect of host Lewis and ABO blood group antigen expression on Helicobacter pylori colonisation density and the consequent inflammatory response. FEMS Immunol Med Microbiol. Apr. 1998;20(4):257-66.
Hurd et al., Increased susceptibility of secretor factor gene Fut2-null mice to experimental vaginal candidiasis. Infect Immun. Jul. 2004;72(7):4279-81.
Ikehara et al., Polymorphisms of two fucosyltransferase genes (Lewis and Secretor genes) involving type I Lewis antigens are associated with the presence of anti-Helicobacter pylori IgG antibody. Cancer Epidemiol Biomarkers Prev. Sep. 2001;10(9):971-7.
Imaoka et al., Anti-inflammatory activity of probiotic Bifidobacterium: enhancement of IL-10 production in peripheral blood mononuclear cells from ulcerative colitis patients and inhibition of IL-8 secretion in HT-29 cells. World J Gastroenterol. Apr. 28, 2008;14(16):2511-6.
Jantscher-Krenn et al., The human milk oligosaccharide disialyllacto-N-tetraose prevents necrotising enterocolitis in neonatal rats. Gut. Oct. 2012;61(10):1417-25. Epub Dec. 3, 2011.
Jiang et al., Prevalence of enteric pathogens among international travelers with diarrhea acquired in Kenya (Mombasa), India (Goa), or Jamaica (Montego Bay). J Infect Dis. Feb. 15, 2002;185(4):497-502. Epub Jan. 22, 2002.
Jimenez, Treatment of irritable bowel syndrome with probiotics. An etiopathogenic approach at last? Rev Esp Enferm Dig. Aug. 2009;101(8):553-64.
Jones et al., Induction of proinflammatory responses in the human monocytic cell line THP-1 by Campylobacter jejuni. Infect Immun. May 2003;71(5):2626-33.
Kafetzis et al., Neonatal necrotizing enterocolitis: an overview. Curr Opin Infect Dis. Aug. 2003;16(4):349-55.
Kim et al., Expression of LeY and extended LeY blood group-related antigens in human malignant, premalignant, and nonmalignant colonic tissues. Cancer Res. Nov. 1986;46(11):5985-92.
Kim et al., Investigating intestinal inflammation in DSS-induced model of IBD. J Vis Exp. Feb. 1, 2012;(60):3678(1-6).
Kim et al., Oligonol prevented the relapse of dextran sulfate sodium-ulcerative colitis through enhancing NRF2-mediated antioxidative defense mechanism. J Physiol Pharmacol. Jun. 2018;69(3):1-13. Epub Aug. 22, 2018.
Klement et al., Breastfeeding and risk of inflammatory bowel disease: a systematic review with meta-analysis. Am J Clin Nutr. Nov. 2004;80(5):1342-52.
Kobayashi et al., Lewis blood group-related antigen expression in normal gastric epithelium, intestinal metaplasia, gastric adenoma, and gastric carcinoma. Am J Gastroenterol. Jun. 1993;88(6):919-24.
Konopka et al., Variable expression of the translocated c-abl oncogene in Philadelphia chromosome-positive B-lymphoid cell lines from chronic myelogenous leukemia patients. Proc Natl Acad Sci U S A. Jun. 1986;83(11):4049-52.
Kunz et al., Oligosaccharides in human milk: structural, functional, and metabolic aspects. Annu Rev Nutr. 2000;20:699-722.
Kunz et al., Potential Anti-Inflammatory and Anti-Infectious Effects of Human Milk Oligosaccharides, Bioactive Components of Milk (Book Series: Advances in Experimental Medicine and Biology, Springer Science & Business Media, New York, NY, US, XP009136897, ISBN: 978-0-387-74086-7: 455-465. 2008.

(56) References Cited

OTHER PUBLICATIONS

Lara-Villoslada et al., Oligosaccharides isolated from goat milk reduce intestinal inflammation in a rat model of dextran sodium sulfate-induced colitis. Clin Nutr. Jun. 2006;25(3):477-88. Epub Jan. 10, 2006.
Le Pendu, Histo-blood group antigen and human milk oligosaccharides: genetic polymorphism and risk of infectious diseases. Adv Exp Med Biol. 2004;554:135-43.
Lee et al., The alteration of enterochromaffin cell, mast cell, and lamina propria T lymphocyte Nos. in irritable bowel syndrome and its relationship with psychological factors. J Gastroenterol Hepatol. Nov. 2008;23(11):1689-94.
Leiper et al., Altered Expression of Fucosyl-Transferases in Inflammatory Bowel Disease. Gastroenterology. 2001;120:A-525, Abstract #2671.
Lewin. Genes VI. Chapter 29—Regulation of transcription. Oxford University Press. 1997: 847-48.
Liebregts et al., Immune Activation in Patients With Irritable Bowel Syndrome. Gastroenterology 2007;132:913-920.
Lin et al., Oral probiotics reduce the incidence and severity of necrotizing enterocolitis in very low birth weight infants. Pediatrics. Jan. 2005;115(1):1-4.
Lucas et al., Breast milk and neonatal necrotising enterocolitis. Lancet. Dec. 22-29, 1990;336(8730):1519-23.
Madjd et al., High expression of Lewis y/b antigens is associated with decreased survival in lymph node negative breast carcinomas. Breast Cancer Res. 2005;7(5):R780-7. Epub Jul. 28, 2005.
Maki, Conversion of GDP-Mannose into Various GDP-Deoxyhexoses in Gram-Negative Bacteria. Academic Dissertation. University of Helsinki, Jun. 16, 2003: 1-63.
Mattila et al., Functional expression of Escherichia coli enzymes synthesizing GDP-L-fucose from inherent GDP-D-mannose in *Saccharomyces cerevisiae*. Glycobiology. Oct. 2000;10(10):1041-7.
Meyrand et al., Comparison of milk oligosaccharides between goats with and without the genetic ability to synthesize $\alpha(s1)$-casein. Small Rumin Res. Jul. 1, 2013;113(2-3):411-420.
Mikhailov et al., Breastfeeding and genetic factors in the etiology of inflammatory bowel disease in children. World J Gastroenterol. Jan. 21, 2009;15(3):270-9.
Morrow et al., Fucosyltransferase 2 non-secretor and low secretor status predicts severe outcomes in premature infants. J Pediatr. May 2011;158(5):745-51. Epub Jan. 22, 2011.
Morrow et al., Human milk oligosaccharide blood group epitopes and innate immune protection against campylobacter and calicivirus diarrhea in breastfed infants. Adv Exp Med Biol. 2004;554:443-6.
Morrow et al., Human milk oligosaccharides are associated with protection against diarrhea in breast-fed infants. J Pediatr. Sep. 2004;145(3):297-303.
Morrow et al., Human-milk glycans that inhibit pathogen binding protect breast-feeding infants against infectious diarrhea. J Nutr. May 2005;135(5):1304-7.
Moss et al., Th1/Th2 cells in inflammatory disease states: therapeutic implications. Expert Opin Biol Ther. Dec. 2004;4(12):1887-96.
Nakamura et al., The milk oligosaccharides of domestic farm animals. Trends in glycolscience glycotechnol. Mar. 2004;16(88):135-142.
Nanthakumar et al., Inflammation in the developing human intestine: A possible pathophysiologic contribution to necrotizing enterocolitis. Proc Natl Acad Sci U S A. May 23, 2000;97(11):6043-8.
Newburg et al., Human milk alpha1,2-linked fucosylated oligosaccharides decrease risk of diarrhea due to stable toxin of *E. coli* in breastfed infants. Adv Exp Med Biol. 2004;554:457-61.
Newburg et al., Human milk glycans protect infants against enteric pathogens. Annu Rev Nutr. 2005;25:37-58.
Newburg et al., Innate protection conferred by fucosylated oligosaccharides of human milk against diarrhea in breastfed infants. Glycobiology. Mar. 2004;14(3):253-63. Epub Nov. 24, 2003. Erratum in: Glycobiology. May 2004;14(5):13G.
Newburg et al., Protection of the neonate by the innate immune system of developing gut and of human milk. Pediatr Res. Jan. 2007;61(1):2-8.
Newburg et al., $\alpha$1,2-linked fucosyloligosaccharides comprise a major component of the innate immune system of human milk. Glycobiology 2003, #233; 13(11):885.
Newburg, Human Milk Glycoconjugates that Inhibit Pathogens. Current Medicinal Chemistry, Bentham Science Publishers BV, BE, vol. 6, No. 2, Jan. 1, 1999: 117-127.
Newburg, Human milk oligosaccharides and glycoconjugates protect the newborn against infection. Pediatric Research. 1999; 45:742. Abstract.
Newburg, Neonatal protection by an innate immune system of human milk consisting of oligosaccharides and glycans. J Anim Sci. Apr. 2009;87(13 Suppl):26-34. Epub Nov. 21, 2008.
O'Mahony et al., Lactobacillus and bifidobacterium in irritable bowel syndrome: symptom responses and relationship to cytokine profiles. Gastroenterology. Mar. 2005;128(3):541-51.
Orlando, The immunologic significance of breast milk. J Obstet Gynecol Neonatal Nurs. Sep. 1995;24(7):678-83.
Papadakis et al., Role of cytokines in the pathogenesis of inflammatory bowel disease. Annu Rev Med. 2000;51:289-98.
Parashar et al., Diarrheal mortality in US infants. Influence of birth weight on risk factors for death. Arch Pediatr Adolesc Med. Jan. 1998;152(1):47-51.
Pennica et al., WISP genes are members of the connective tissue growth factor family that are up-regulated in wnt-1-transformed cells and aberrantly expressed in human colon tumors. Proc Natl Acad Sci U S A. Dec. 8, 1998;95(25):14717-22.
Podolsky et al., Development of anti-human colonic mucin monoclonal antibodies. Characterization of multiple colonic mucin species. J Clin Invest. Apr. 1986;77(4):1251-62.
Pradel et al., Prevalence and characterization of Shiga toxin-producing *Escherichia coli* isolated from cattle, food, and children during a one-year prospective study in France. J Clin Microbiol. Mar. 2000;38(3):1023-31.
Prestwich et al., Controlled chemical modification of hyaluronic acid: synthesis, applications, and biodegradation of hydrazide derivatives. J Control Release. Apr. 30, 1998;53(1-3):93-103.
Prieto, In vitro and clinical experiences with a human milk oligosaccharide, Lacto-N-neotetraose, and fructooligosaccharides. Foods Food Ingredients J Jpn. 2005;210(11):1018-1029.
Qin et al., Systematic review of animal models of post-infectious/post-inflammatory irritable bowel syndrome. J Gastroenterol. Feb. 2011;46(2):164-74. Epub Sep. 17, 2010.
Redmond et al., The use of solid-phase extraction with graphitised carbon for the fractionation and purification of sugars. Carbohydrate Research. 1999;319:74-79.
Rivero et al., Effect of a new infant formula enriched with prebiotics, probiotics, nucleotides and LC-PUFA on recovery after infection. Advances in Experimental Medicine and Biology. 2005;569:186-7.
Rubaltelli et al., Feeding and Neonatal Necrotizing Enterocolitis. In: Nutrition of the Very Low Birthweight Infant. Eds: Ziegler et al. 1999. 199-210.
Rudloff et al., Detection of ligands for selectins in the oligosaccharide fraction of human milk. Eur J Nutr. Apr. 2002;41(2):85-92.
Ruiz-Palacios et al., Campylobacter jejuni binds intestinal H(O) antigen (Fuc alpha 1, 2Gal beta 1, 4GlcNAc), and fucosyloligosaccharides of human milk inhibit its binding and infection. J Biol Chem. Apr. 18, 2003;278(16):14112-20. Epub Jan. 31, 2003.
Saiman et al., Risk factors for candidemia in Neonatal Intensive Care Unit patients. The National Epidemiology of Mycosis Survey study group. Pediatr Infect Dis J. Apr. 2000;19(4):319-24.
Schnabl et al. Necrotizing enterocolitis: a multifactorial disease with no cure. World J Gastroenterol. Apr. 14, 2008;14(14):2142-61.
Sharon et al., Safe as mother's milk: carbohydrates as future anti-adhesion drugs for bacterial diseases. Glycoconj J. Jul.-Sep. 2000;17(7-9):659-64.
Sisk et al., Early human milk feeding is associated with a lower risk of necrotizing enterocolitis in very low birth weight infants. J Perinatol. Jul. 2007;27(7):428-33. Epub Apr. 19, 2007. Erratum in: J Perinatol. Dec. 2007;27(12):808.

(56) References Cited

OTHER PUBLICATIONS

Smith et al., Postinfectious irritable bowel syndrome: a long-term consequence of bacterial gastroenteritis. J Food Prot. Jul. 2007;70(7):1762-9.

Snelling, Effects of probiotics on the gastrointestinal tract. Curr Opin Infect Dis. Oct. 2005;18(5):420-6.

Spik et al., Primary and three-dimensional structure of lactotransferrin (lactoferrin) glycans. PP 21-32 from Lactoferrin: Structure and Function, T.W. Hutchens, ed. Plenum Press, New York, 1994.

Spik et al., Primary structure of the glycans from human lactotransferrin. Eur J Biochem. Jan. 1982;121(2):413-9.

Spiller et al., Increased rectal mucosal enteroendocrine cells, T lymphocytes, and increased gut permeability following acute Campylobacter enteritis and in post-dysenteric irritable bowel syndrome. Gut. Dec. 2000;47(6):804-11.

Spiller et al., Infection, inflammation, and the irritable bowel syndrome. Dig Liver Dis. Dec. 2009;41(12):844-9. Epub Aug. 28, 2009.

Strömqvist et al., Human milk kappa-casein and inhibition of Helicobacter pylori adhesion to human gastric mucosa. J Pediatr Gastroenterol Nutr. Oct. 1995;21(3):288-96.

Thomsson et al., MUC5B glycosylation in human saliva reflects blood group and secretor status. Glycobiology. Aug. 2005;15(8):791-804. Epub Apr. 6, 2005.

Thurl et al., Quantification of individual oligosaccharide compounds from human milk using high-pH anion-exchange chromatography. Anal Biochem. Mar. 15, 1996;235(2):202-6.

Treszl et al., Genetic basis for necrotizing enterocolitis—risk factors and their relations to genetic polymorphisms. Front Biosci. Jan. 1, 2006;11:570-80.

Tsuboi et al., Alpha1,2fucosylation is a superior predictor of postoperative prognosis for colorectal cancer compared with blood group A, B, or sialyl Lewis X antigen generated within colorectal tumor tissues. Ann Surg Oncol. Jun. 2007;14(6):1880-9. Epub Mar. 21, 2007.

Urashima et al., Oligosaccharides of milk and colostrum in non-human mammals. Glycoconj J. May 2001;18(5):357-71.

Urashima et al., Recent advances in studies on milk oligosaccharides of cows and other domestic farm animals. Biosci Biotechnol Biochem. 2013;77(3):455-66. Epub Mar. 7, 2013.

Urashima et al., Studies of the neutral trisaccharides of goat (*Capra hircus*) colostrum and of the one- and two-dimensional 1H and 13C NMR spectra of 6'-N-acetylglucosaminyllactose. Carbohydr Res. Sep. 15, 1994;262(2):173-84.

Velupillai et al., Oligosaccharide-specific induction of interleukin 10 production by B220+ cells from schistosome-infected mice: a mechanism for regulation of CD4+ T-cell subsets. Proc Natl Acad Sci U S A. Jan. 4, 1994;91(1):18-22.

Wakabayashi et al., Lactoferrin research, technology and applications. Int Dairy J. 2006; 16:1241-51.

Ward, Isolation of Milk Oligosaccharides using solid-phase extraction. Open Glycoscience. 2009;2:9-15.

Wheatcroft et al., Enterochromaffin cell hyperplasia and decreased serotonin transporter in a mouse model of postinfectious bowel dysfunction. Neurogastroenterol Motil. Dec. 2005;17(6):863-70.

Wilson et al., Glycoproteomics of milk: differences in sugar epitopes on human and bovine milk fat globule membranes. J Proteome Res. Sep. 2008;7(9):3687-96. Epub Jul. 15, 2008.

Wu et al., Identification and characterization of GDP-d-mannose 4,6-dehydratase and GDP-l-fucose snthetase in a GDP-l-fucose biosynthetic gene cluster from Helicobacter pylori. Biochem Biophys Res Commun. Jul. 13, 2001;285(2):364-71.

Yolken et al., Human milk mucin inhibits rotavirus replication and prevents experimental gastroenteritis. J Clin Invest. Nov. 1992;90(5):1984-91.

Ziemer et al., An Overview of Probiotics, Prebiotics and Synbiotics in the Functional Food Concept: Perspectives and Future Strategies. Int Dairy J. 1998; 8:473-79.

\* cited by examiner

INHIBITING INFLAMMATION WITH MILK OLIGOSACCHARIDES

CROSS-REFERENCE TO RELATED APPLICATIONS

This application is a continuation of U.S. patent application Ser. No. 17/333,614, filed May 28, 2021, which is a continuation of U.S. patent application Ser. No. 15/998,799, filed Aug. 16, 2018, now U.S. Pat. No. 11,058,697, which is a continuation of U.S. patent application Ser. No. 14/700,232, filed Apr. 30, 2015, now U.S. Pat. No. 10,098,903, which is a continuation of U.S. patent application Ser. No. 13/382,323, filed Mar. 26, 2012, now U.S. Pat. No. 9,034,847, which is a national stage filing under 35 U.S.C. 371 of International Patent Application Serial No. PCT/US2010/040895, filed Jul. 2, 2010, which claims the benefit of U.S. Provisional Application No. 61/223,145 filed on Jul. 6, 2009. The content of each of the prior application is hereby incorporated by reference in its entirety.

GOVERNMENT SUPPORT

This invention was made with government support under HD013021 awarded by the National Institutes of Health. The government has certain rights in the invention.

BACKGROUND OF THE INVENTION

Various components in human milk, e.g., milk immunoglobulins, leukocytes, oligosaccharides, and glycoconjugates, protect infants against infectious diseases. Human milk is thus considered a natural efficacious "nutriceutical," i.e., a model food that conveys immunologic benefits.

Human milk has also been found to reduce the risk of developing inflammatory enteric diseases in infants. This anti-inflammation activity has been attributed to the leukocytes, cytokines, and antioxidants in human milk. See Buescher, Adv Exp Med Biol. 501:207-22 (2001).

SUMMARY OF THE INVENTION

The present invention is based on an unexpected discovery that oligosaccharides in human milk inhibit inflammation.

Accordingly, one aspect of this invention features a method of inhibiting inflammation by administering to a subject in need thereof an effective amount of a composition containing one or more milk-derived oligosaccharides or one or more glycoconjugates containing the oligosaccharide(s). A milk-derived oligosaccharide contains a first sugar unit (i.e., fucose, galactose, mannose, or sialic acid), which is located at a non-reducing end of the oligosaccharide, and a second sugar unit (i.e., galactose, glucose, mannose, or N-acetylglucosamine), which is directly linked to the first sugar unit. In one example, the oligosaccharide is a linear molecule having one non-reducing end and one reducing end. In another example, it is a branched molecule having multiple non-reducing ends and one reducing end. When the oligosaccharide has two non-reducing ends, the sugar unit at one non-reducing end can be fucose and that at the other non-reducing end can be fucose, galactose, or sialic acid, or alternatively, the sugar unit at one non-reducing end is sialic acid and that at the other non-reducing end is galactose or sialic acid. The sugar unit at the reducing end can be a glucose or an N-acetylglucosamine.

The glycoconjugate(s) used in the method described above can include one or more of the milk-derived oligosaccharide(s) also described above conjugated with a lipid, a peptide, a polypeptide, or a carbohydrate.

Another aspect of this invention features a method of inhibiting inflammation with oligosaccharides isolated from milk, which can be derived from a human, a bovid (e.g., a cow, a goat, or a sheep), or another mammal (e.g., a horse or a camel). The oligosaccharides can be prepared by first removing fat and protein from the milk before its isolation via conventional methods. In one example, after removal of fat and protein, the milk is loaded onto a carbon column and the oligosaccharides adsorbed onto the column are eluted with an alcohol solution (e.g., a 50% aqueous ethanol solution).

The method of this invention can be applied to a subject, e.g., a human or a non-human mammal, who is suffering from or at risk for developing an inflammatory disease, such as a disease of the digestive tract. Examples include oesophagitis, gastroenteritis, colitis, cholangitis, appendicitis, inflammatory bowel diseases (i.e., ulcerative colitis, necrotizing enterocolitis, and Crohn's disease), or irritable bowel syndrome.

Also within the scope of this invention is use of one or more milk-derived oligosaccharides or one or more glycoconjugates containing the oligosaccharide(s) for inhibiting inflammation and for the manufacture of a medicament for treating inflammatory diseases.

The details of one or more embodiments of the invention are set forth in the description below. Other features or advantages of the present invention will be apparent from the following drawings and detailed description of an example, and also from the appended claims.

DETAILED DESCRIPTION OF THE INVENTION

Figure 1:
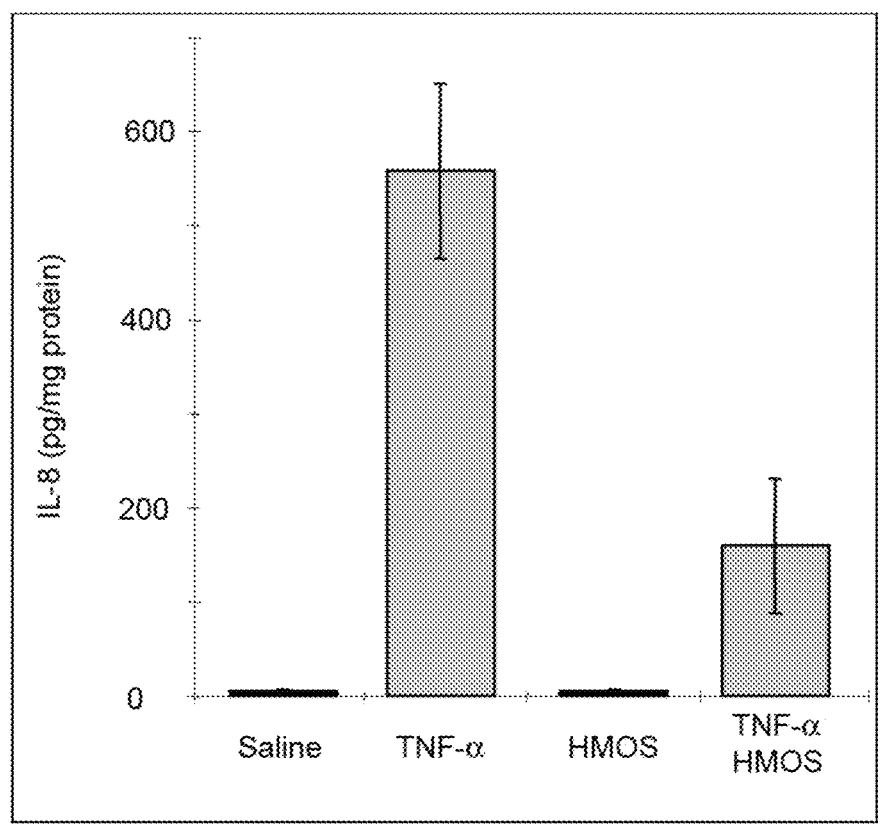
FIG. 1 is a chart showing that human milk oligosaccharides inhibit TNF-α induced IL-8 production by T84 enterocytes.

Disclosed herein is a method of inhibiting inflammation with one or more milk-derived oligosaccharides or one or more glycoconjugates containing the oligosaccharides.

A milk-derived oligosaccharide, i.e., having at least three sugar units, is either a naturally-occurring oligosaccharide found in milk, a fragment of the naturally-occurring oligosaccharide, or a variant thereof that contains a modified (e.g., sulfated, acetylated, or phosphorylated) sugar unit as compared to its natural counterpart. This oligosaccharide includes a non-reducing end motif $S_1S_2$, in which $S_1$ is fucose, galactose, mannose, or sialic acid (N-acetyl or N-glycolyl) and $S_2$ is galactose, glucose, mannose, or N-acetylglucosamine. $S_1$ is linked to $S_2$ via an α or β glycosidic bond. When $S_1$ is fucose, the glycosidic bond between $S_1$ and $S_2$ preferably is an α1,2, an α1,3, or an α1,4 bond. When it is sialic acid, the glycosidic bond preferably is an α2,3 or an α2,6 bond.

Milk-derived oligosaccharides and glycoconjugates containing such oligosaccharides are well known in the art. See, e.g., U.S. Patent Application 61/168,674 and WO2005/055944. The following tables list exemplary oligosaccharides that naturally occur in human milk:

TABLE 1

| | Fucosyl oligosaccharides | |
|---|---|---|
| 2'FL | 2-Fucosyllactose | Fucα1,2Galβ1,4Glc |
| LNF-I | Lacto-N-fucopentaose I | Fucα1,2Galβ1,3GlcNAcβ1,3Galβ1,4Glc |
| LNF-II | Lacto-N-fucopentaose II | Galβ1,3 ↘<br>　　　GlcNAcβ1,3Galβ1,4Glc<br>Fucα1,4 ↗ |
| 3'FL | 3-Fucosyllactose | Galβ1,4 ↘<br>　　　Glc<br>Fucα1,3 ↗ |

TABLE 1-continued

| | Fucosyl oligosaccharides | |
|---|---|---|
| LNF-III | Lacto-N-fucopentaose III | Galβ1,4 ↘<br>　　　GlcNAcβ1,3Galβ1,4Glc<br>Fucα1,3 ↗ |
| LDFH-I | Lacto-N-difucohexaose I | Fucα1,2Galβ1,3 ↘<br>　　　GlcNAcβ1,3Galβ1,4Glc<br>Fucα1,4 ↗ |
| LDFT | Lactodifucotetraose | Fucα1,2Galβ1,4 ↘<br>　　　Glc<br>Fucα1,3 ↗ |

TABLE 2

| | Nonfucosylated, nonsialylated oligosaccharides | |
|---|---|---|
| LNT | Lacto-N-tetraose | Galβ1, 3GlcNAcβ1, 3Galβ1, 4Glc |
| LNneoT | Lacto-N-neotetraose | Galβ1, 4GlcNAcβ1, 3Galβ1, 4Glc |

TABLE 3

| | Sialyl milk oligosaccharide structures | |
|---|---|---|
| 3'-SL | 3'-Sialyllactose | NANAα2,3Galβ1,4Glc |
| 6'-SL | 6'-Sialyllactose | NANAα2,6Galβ1,4Glc |
| SLNT-c | Sialyllacto-N-neotetraose c | NANAα2,6Galβ1,4GlcNAcβ1,3Galβ1,4Glc |
| MSLNH | Monosialyllacto-N-hexaose | NANAα2,6Galβ1,4GlcNAc1,6 ↘<br>　　　Galβ1,4Glc<br>Galβ1,3GlcNAcβ1,3 ↗ |
| DSLNH-I | Disialyllacto-N-hexaose I | NANAα2,3Galβ1,3GlcNAcβ1,3 ↘<br>　　　Galβ1,4Glc<br>NANAα2,6Galβ1,4GlcNAcβ1,6 ↗ |
| MSLNnH-I | Monosialyllacto-N-neohexaose I | NANAα2,6Galβ1,3GlcNAcβ1,3 ↘<br>　　　Galβ1,4Glc<br>Galβ1,4GlcNAcβ1,6 ↗ |
| SLNnH-II | Monosialyllacto-N-neohexaose II | Galβ1,4GlcNAcβ1,3 ↘<br>　　　Galβ1,4Glc<br>NANAα2,6Galβ1,4GlcNAcβ1,6 ↗ |
| DSLNnH | Disialyllacto-N-neohexaose | NANAα2,6Galβ1,4GlcNAcβ1,3 ↘<br>　　　Galβ1,4Glc<br>NANAα2,6Galβ1,4GlcNAcβ1,6 ↗ |
| DSLNT | Disialyllacto-N-tetraose | NANAα2,6 ↘<br>　　　GlcNAcβ1,3Galβ1,4Glc<br>NANAα2,3Galβ1,3 ↗ |

TABLE 3-continued

Sialyl milk oligosaccharide structures

| | | |
|---|---|---|
| DSLNH-II | Disialyllacto-N-hexaose II | NANAα2,6↘<br>　　　　GlcNAcβ1,3↘<br>NANAα2,3Galβ1,3↗　　Galβ1,4Glc<br>　　Galβ1,4GlcNAcβ1,6↗ |
| SLNT-a | Sialyllacto-N-tetraose a | NANAα2,3Galβ1,3GlcNAcβ1,3Galβ1,4Glc |
| DSLNH-I | Disialyllacto-N-hexaose I | NANAα2,3Galβ1,3GlcNAcβ1,3↘<br>　　　　　　Galβ1,4Glc<br>NANAα2,6Galβ1,4GlcNAcβ1,6↗ |
| SLNT-b | Sialyllacto-N-tetraose b | NANAα2,6↘<br>　　GlcNAcβ1,3Galβ1,4Glc<br>Galβ1,3↗ |

TABLE 4

Sialyl fucosyl oligosaccharides

| | | |
|---|---|---|
| 3'-S-3FL | 3'-Sialyl-3-fucosyllactose | NANAα2,3Galβ1,4↘<br>　　　Glc<br>　Fucα1,3↗ |
| DSFLNH | Disialomonofucosyllacto-N-neohexaose | NANAα2,6Galβ1,4GlcNAcβ1,6↘<br>Fucα1,3↘　　　Galβ1,4Glc<br>　　GlcNAcβ1,3↗<br>NANAα2,6Galβ1,4↗ |
| MFMSLNO | Monofucosylmonosialyllacto-N-octaose (sialyl Lea) | Galβ1,4GlcNAcβ1,3Galβ1,4GlcNAcβ1,6↘<br>　　　　　　　Galβ1,4Glc<br>　NANAα2,3Galβ1,3GlcNAcβ1,3↗<br>　　　Fucα1,4↗ |
| SLNFH-II | Sialyllacto-N-fucohexaose II | NANAα2,3Galβ1,3GlcNAcβ1,3Galβ1,4Glc<br>　　Fucα1,4↗　　Fucα1,3↗ |
| DSLNFP-II | Disialyllacto-N-fucopentaose II | NANAα2,6↘<br>NANAα2,3Galβ1,3GlcNAcβ1,3Galβ1,4Glc<br>　　Fucα1,4↗ |
| MFDLNT | Monofucosyldisialyllacto-N-tetraose | NANAα2,6↘<br>NANAα2,3Galβ1,3GlcNAcβ1,3Galβ1,4Glc<br>　　Fucα1,4↗ |

The milk-derived oligosaccharides described herein can be prepared by conventional methods, e.g., synthesized chemically, purified from milk, or produced in a microorganism. See WO2005/055944. Below is an example of isolating oligosaccharides from milk. Milk is first defatted by centrifugation to produce skimmed milk. The skimmed milk is then mixed with an organic solvent, such as acetone (e.g., 50% aqueous acetone) and ethanol (e.g., 67% aqueous ethanol), to precipitate milk proteins. Upon centrifugation, the supernatant is collected and subjected to chromatography. Oligosaccharide-containing fractions are collected and pooled. If necessary, the oligosaccharides thus prepared can be concentrated by conventional methods, e.g., dialysis or freeze-drying.

Milk oligosaccharides can also be isolated from skimmed milk by passing the skimmed milk through a 30,000 MWCO ultrafiltration membrane, collecting the diffusate, passing the diffusate through a 500 MWCO ultrafilter, and collecting the retentate, which contains milk oligosaccharides.

The glycoconjugates described herein, containing one or more milk-derived oligosaccharides, can be chemically synthesized by conjugating the oligosaccharide(s) to a backbone molecule (e.g., a carbohydrate, a lipid, a nucleic acid, or a peptide) directly or via a linker. As used herein, "glycoconjugate" refers to a complex containing a sugar moiety associated with a backbone moiety. The sugar and the backbone moieties can be associated via a covalent or noncovalent bond, or via other forms of association, such as entrapment (e.g., of one moiety on or within the other, or of either or both entities on or within a third moiety). The glycoconjugate described herein can contain one type of milk-derived oligosaccharide (i.e., one or more copies of a milk-derived oligosaccharide attached to one backbone molecule). Alternatively, the glycoconjugate contains multiple types of milk-derived oligosaccharides. In one example, the milk-derived oligosaccharide (e.g., lacto-N-fucopentaose I, 2-fucosyllactose, lacto-N-difucohexaose I, lactodifucotetraose, or an acetylated variant thereof) is covalently linked via its reducing end sugar unit to a lipid, a protein, a nucleic acid, or a polysaccharide. Preferably, the reducing end sugar unit is N-acetylglucosamine.

Peptide backbones suitable for making the glycoconjugate described above include those having multiple glycosylation sites (e.g., asparagine, lysine, serine, or threonine residue) and low allergenic potential. Examples include, but are not limited to, amylase, bile salt-stimulated lipase, casein, folate-binding protein, globulin, gluten, haptocorrin, lactalbumin, lactoferrin, lactoperoxidase, lipoprotein lipase, lysozyme, mucin, ovalbumin, and serum albumin.

Typically, a milk-derived oligosaccharide can be covalently attached to a serine or threonine residue via an O-linkage or attached to an asparagine residue via an N-linkage. To form these linkages, the sugar unit at the reducing end of the oligosaccharide is preferably an acetylated sugar unit, e.g., N-acetylgalactosamine, N-acetylglucosamine, and N-acetylmannosamine. An oligosaccharide can be attached to a peptide (e.g., a protein) using standard methods. See, e.g., McBroom et al., *Complex Carbohydrates, Part B*, 28:212-219, 1972; Yariv et al., *Biochem J.*, 85:383-388, 1962; Rosenfeld et al., *Carbohydr. Res.*, 46:155-158, 1976; and Pazur, *Adv. Carbohydr. Chem, Biochem.*, 39:405-447, 1981.

In one example, a milk-derived oligosaccharide is linked to a backbone molecule via a linker. Exemplary linkers are described in WO2005/055944. The oligosaccharide can be bonded to a linker by an enzymatic reaction, e.g., a glycosyltransferase reaction. A number of glycosyltransferases, including fucosyltransferases, galactosyltransferases, glucosyltransferases, mannosyltransferases, galactosaminyltransferases, sialyltransferases and N-acetylglucosaminyltransferases, can be used to make the glycoconjugate described herein. More details about these glycosyltransferases can be found in U.S. Pat. Nos. 6,291,219; 6,270,987; 6,238,894; 6,204,431; 6,143,868; 6,087,143; 6,054,309; 6,027,928; 6,025,174; 6,025,173; 5,955,282; 5,945,322; 5,922,540; 5,892,070; 5,876,714; 5,874,261; 5,871,983; 5,861,293; 5,859,334; 5,858,752; 5,856,159; and 5,545,553.

Alternatively, the glycoconjugates described herein can be purified from milk by conventional methods e.g., by passing through ultrafiltration membranes, by precipitation in non-polar solvents, or through partition between immiscible solvents.

One or more of the above-described milk oligosaccharides or glycoconjugates can be mixed with a pharmaceutically acceptable carrier to form a pharmaceutical composition. The carrier in the pharmaceutical composition must be "acceptable" in the sense of being compatible with the active ingredient of the formulation (and preferably, capable of stabilizing it) and not deleterious to the subject to be treated. For example, solubilizing agents such as cyclodextrins, which form more soluble complexes with the oligosaccharides/glycoconjugates, or more solubilizing agents, can be utilized as pharmaceutical carriers for delivery of the oligosaccharides/glycoconjugates. Examples of other carriers include colloidal silicon dioxide, magnesium stearate, sodium lauryl sulfate, and D&C Yellow #10.

Alternatively, the oligosaccharides/glycoconjugates can also be formulated as food produces or food supplements following methods well known in the food industry. In one example, they are components of infant formulas.

The oligosaccharides and glycoconjugates are effective in inhibiting inflammation and treating inflammation-associated diseases (i.e., inflammatory diseases) Inflammation is reaction of living tissue (e.g., heat, redness, swelling, or pain) in response to injury or infection. Exemplary inflammation-associated diseases, characterized by a local or systemic, acute or chronic inflammation, include inflammatory retinopathy (e.g., diabetic retinopathy), dermatoses (e.g., dermatitis, eczema, atopic dermatitis, allergic contact dermatitis, urticaria, necrotizing vasculitis, cutaneous vasculitis, hypersensitivity vasculitis, eosinophilic myositis, polymyositis, dermatomyositis, and eosinophilic fasciitis), hypersensitivity lung diseases (e.g., hypersensitivity pneumonitis, eosinophilic pneumonia, delayed-type hypersensitivity, interstitial lung disease or ILD, idiopathic pulmonary fibrosis, and ILD associated with rheumatoid arthritis), asthma, and allergic rhinitis. In addition to treating the above-listed inflammatory diseases, the method of this invention is particularly effective in treating inflammatory disease of the digestive tract, including oesophatigis (i.e., inflammation of the oesophagus, such as oesophageal ulcer), gastroenteritis (i.e., inflammation of the mucous membranes of the stomach and intestine, such as gastritis, duodenal ulcer, ileitis, or enterocolitis), colitis (i.e., inflammation of the colon, such as diverticulitis), cholangitis (i.e., inflammation of the bile duct), and appendicitis (i.e., inflammation of the appendix) Inflammatory disease of the digestive tract also includes inflammatory bowel diseases (e.g., Crohn's disease and ulcerative colitis) and irritable bowel syndrome.

The term "treating" as used herein refers to the application or administration of a composition including one or more active agents to a subject, who has an inflammatory disease, a symptom of the inflammatory disease, or a predisposition toward the inflammatory disease, with the purpose to cure, heal, alleviate, relieve, alter, remedy, ameliorate, improve, or affect the disease, the symptoms of the disease, or the predisposition toward the disease.

To practice the method of this invention, an effective amount of the above-described pharmaceutical composition can be administered to a subject (e.g., a human infant or elderly) orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. "An effective amount" as used herein refers to the amount of each active agent required to confer therapeutic effect on the subject, either alone or in combination with one or more other active agents. Effective amounts vary, as recognized by those skilled in the art, depending on route of administration, excipient usage, and co-usage with other active agents.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well known in the art of pharmaceutical formulation.

Suitable in vitro and in vivo assays can be used to preliminarily evaluate the anti-inflammation activity of a particular milk oligosaccharide or a combination of various milk oligosaccharides. For example, the oligosaccharide(s) can be tested in vitro for its ability of inhibiting secretion of pro-inflammatory cytokines (e.g., IL-1, IL-6, TNF-alpha GM-CSF, IL-8, and IL-12). The anti-inflammation activity can further be confirmed in an animal model (e.g., a mouse model). Based on the results, an appropriate dosage range and administration route can also be determined.

Without further elaboration, it is believed that one skilled in the art can, based on the above description, utilize the present invention to its fullest extent. The following specific example is therefore to be construed as merely illustrative, and not limitative of the remainder of the disclosure in any way whatsoever. All publications cited herein are incorporated by reference.

Use of Human Milk Oligosaccharides for Inhibiting Intestinal Inflammation

Preparation of Human Milk Oligosaccharides

An oligosaccharide fraction was isolated from human milk following the method described in Chaturvedi et al., Anal. Biochem. 251(1):89-97, 1997. Briefly, pooled human milk was first defatted and then ethanol was added to precipitate proteins. The resultant solution was loaded onto a carbon column, which adsorbs oligosaccharides. The column was washed with 5% ethanol and the adsorbed oligosaccharides were eluted with 60% ethanol to produce a fraction containing human milk oligosaccharides ("HMOS").

HMOS Inhibit IL-8 Secretion in TNF-Treated T84 Cells

T84 cells, used routinely for studying neonatal epithelial inflammation, were cultured in 24-well Falcon organ culture dishes at 37° C. with 95% $O_2$ and 5% $CO_2$ in DMEM/F12 medium supplemented with FBS (5%), Hepes buffer, NaOH, penicillin and streptomycin. These cells were treated with (i) saline as a negative control, (ii) TNF-α (10 ng/mL) as a positive control, (iii) HMOS (5 g/L), and (iv) TNF-α (10 ng/mL) and HMOS (5 g/L). After 16 hours, the concentration of IL-8 in each culture supernatant was measured by ELISA. The results thus obtained were standardized to the cell numbers (i.e., divided by the total cell protein contents of the corresponding cell cultures).

As shown in FIG. 1, the TNF-induced IL-8 production was significantly reduced in HMOS-treated T84 cells, indicating that HMOS exhibited anti-inflammatory activity.

HMOS Inhibit Monocyte Chemoattractant Protein-1 (MCP-1) Secretion in Human Intestinal Mucosa Human small intestine mucosa samples from 14 wk abortuses were incubated in 24-well Falcon organ culture plates with CMRL 1066 medium supplemented with FBS (5%), glucose (5 g/L), tricine buffer (20 mM, pH 7.4), hydrocortisone hemisuccinate (0.5 µg/L), β-retinyl acetate (1 mg/L), penicillin and streptomycin in 5% $CO_2$ at 37° C. The mucosa samples were treated with (i) saline as a negative control, (ii) TNF-α (10 ng/mL) as a positive control, (iii) HMOS (5 g/L), and (iv) TNF-α (10 ng/mL) and HMOS (5 g/L). After 16 hours, the concentration of MCP-1, a pro-inflammatory chemokine, was measured in each culture supernatant by ELISA. The results thus obtained were standized to cell numbers as described above.

Figure 2:
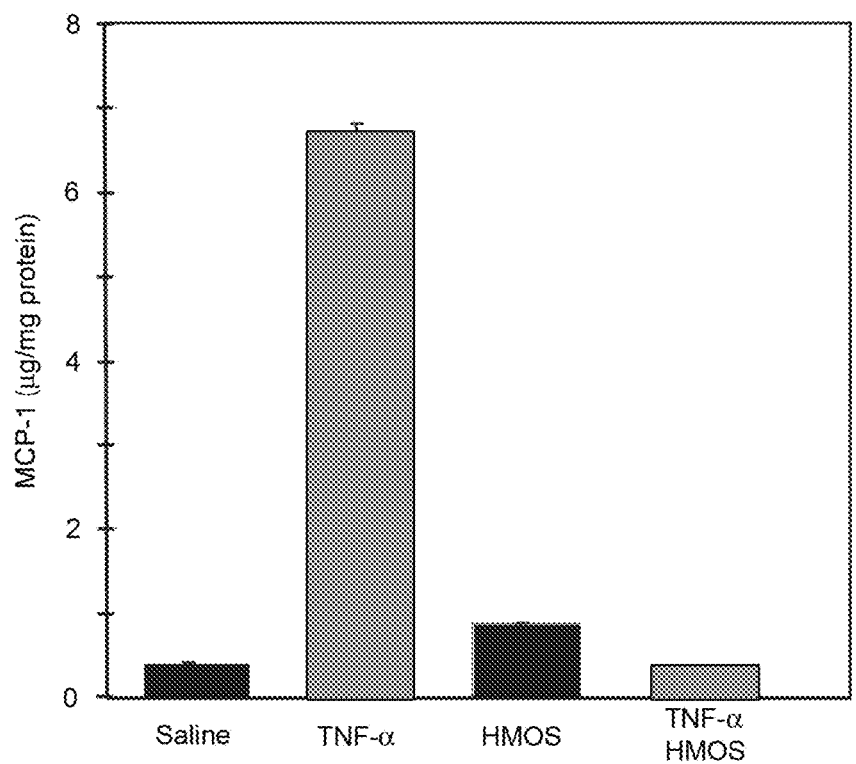
FIG. 2 is a chart showing that human milk oligosaccharides inhibit TNF-α induced monocyte chemoattractant protein-1 production by human intestinal mucosa.

The data obtained from this study, shown indicate that in the presence of TNF-α, human intestinal mucosa secreted a high level of MCP-1, a measure of inflammation and this TNF-α induced MCP-1 production was attenuated by HMOS. See FIG. 2.

Inhibition of IL-8 Secretion in Organ Culture of Immature Human Intestinal Mucosa Human small intestine samples from 22 wk abortuses were incubated in 24-well plates with the modified CMRL media described above in 5% $CO_2$ at 37° C. The samples were treated with IL-1β (10 ng/mL), flagellin (1 mg/mL), polyinosinic-polycytidilic double stranded RNA (PIC; 10 ng/mL), or PBS (as a negative control) in the absence or presence of 5 mg/mL HMOS for 18 h. Levels of IL-8 secretion in the culture supernatants were measured using a ELISA kit (R & D Systems) in duplicate, with detection at 450 nm on a versa max plate reader (Molecular Devices, CA, USA). Each $OD_{450}$ value was normalized to the total protein amount of the corresponding organ culture.

Figure 3:
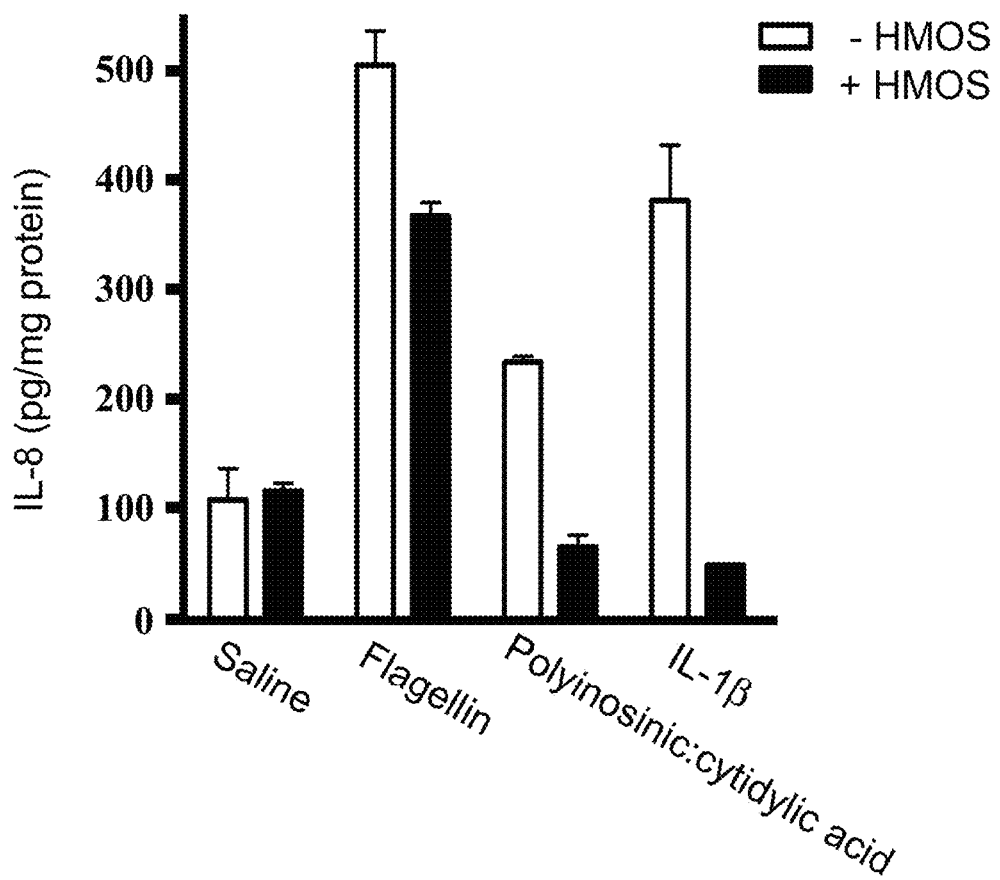
FIG. 3 is a chart showing that flagelin, polyinosinic-polycytidilic double-stranded RNA, or IL-1β induces IL-8 production in organ culture of immature human intestinal mucosa and human milk oligosaccharides inhibit this induced IL-8 production.

Flagelin, polyinosinic-polycytidilic double stranded RNA, and IL-1β all induced a pro-inflammatory response, as evidenced by secretion of IL-8. See FIG. 3. This pro-inflammatory response was significantly attenuated by HMOS.

Take together, the results shown above indicate that milk oligosaccharides are effective in inhibiting inflammation.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of inhibiting inflammation in a subject, comprising administering to a subject a composition comprising one or more milk-derived oligosaccharides, which comprise a fucose residue; wherein the composition is free of oligosaccharides which comprise a sialic acid residue, fat and protein; and wherein the subject is suffering from irritable bowel syndrome (IBS), ulcerative colitis, or Crohn's disease.

2. The method of claim 1, wherein the one or more milk-derived oligosaccharides are synthesized chemically or produced by a microorganism.

3. The method of claim 1, wherein secretion of one or more pro-inflammatory cytokines is reduced in the subject.

4. The method of claim 3, wherein the one or more pro-inflammatory cytokines is selected from the group consisting of IL-1, IL-6, TNF-alpha, GM-CSF, IL-8 and IL-12.

5. The method of claim 1, wherein the subject is a human IBS patient and wherein pain is reduced in the subject.

6. The method of claim 1, wherein the composition is an oral formulation.

7. A method of treating irritable bowel syndrome (IBS), comprising administering to a subject suffering from IBS a composition comprising one or more milk-derived oligosaccharides, which comprise a fucose residue; and wherein the composition is free of oligosaccharides which comprise a sialic acid residue, fat and protein.

8. The method of claim 7, wherein the one or more milk-derived oligosaccharides are synthesized chemically or produced by a microorganism.

9. The method of claim 7, wherein secretion of one or more pro-inflammatory cytokines is reduced in the subject.

10. The method of claim 9, wherein the one or more pro-inflammatory cytokines is selected from the group consisting of IL-1, IL-6, TNF-alpha, GM-CSF, IL-8 and IL-12.

11. The method of claim 7, wherein pain is reduced in the subject.

12. The method of claim 7, wherein the composition is an oral formulation.

13. The method of claim 7, wherein the subject is a human IBS patient.

14. The method of claim 1, wherein the one or more human milk-derived oligosaccharides comprise 2-fucosyllactose (2'-FL), lacto-N-fucopentaose I (LNF-I), lacto-N-fucopentaose II (LNF-II), 3-fucosyllactose (3-FL), lacto-N-fucopentaose III (LNF-III), lacto-N-difucohexaose I (LDFH-I), lactodifucotetraose (LDFT), or a combination thereof.

15. The method of claim 14, wherein the one or more human milk-derived oligosaccharides comprise 2'-FL.

16. The method of claim 14, wherein the one or more human milk-derived oligosaccharides further comprise lacto-N-tetraose (LNT), lacto-N-neotetraose (LNneoT), or a combination thereof.

17. The method of claim 1, wherein the one or more milk-derived oligosaccharides are prepared by a process comprising:
 (a) removing fat and protein from milk;
 (b) isolating oligosaccharides from the milk after step (a);
 (c) loading the oligosaccharides isolated in step (b) onto a carbon column; and
 (d) eluting the one or more milk-derived oligosaccharides from the carbon column with an alcohol solution.

18. The method of claim 7, wherein the one or more human milk-derived oligosaccharides comprise 2-fucosyllactose (2'-FL), lacto-N-fucopentaose I (LNF-I), lacto-N-fucopentaose II (LNF-II), 3-fucosyllactose (3-FL), lacto-N-fucopentaose III (LNF-III), lacto-N-difucohexaose I (LDFH-I), lactodifucotetraose (LDFT), or a combination thereof.

19. The method of claim 18, wherein the one or more human milk-derived oligosaccharides comprise 2'-FL.

20. The method of claim 18, wherein the one or more human milk-derived oligosaccharides further comprise lacto-N-tetraose (LNT), lacto-N-neotetraose (LNneoT), or a combination thereof.

21. The method of claim 7, wherein the one or more milk-derived oligosaccharides are prepared by a process comprising:
 (a) removing fat and protein from milk;
 (b) isolating oligosaccharides from the milk after step (a);
 (c) loading the oligosaccharides isolated in step (b) onto a carbon column; and
 (d) eluting the one or more milk-derived oligosaccharides from the carbon column with an alcohol solution.

* * * * *